(12) United States Patent
Klepetko

(10) Patent No.: US 11,484,691 B2
(45) Date of Patent: *Nov. 1, 2022

(54) CANNULA ASSEMBLY FOR FITTING A FLOW CANNULA FOR INTRODUCING, CIRCULATING OR DIVERTING FLOW MEDIA, AND METHOD FOR EXTRACORPOREAL SUPPORT OF A PATIENT WITH PULMONARY HYPERTENSION OR PULMONARY INSUFFICIENCY

(71) Applicant: Walter Klepetko, Vienna (AT)

(72) Inventor: Walter Klepetko, Vienna (AT)

( * ) Notice: Subject to any disclaimer, the term of this patent is extended or adjusted under 35 U.S.C. 154(b) by 681 days.

This patent is subject to a terminal disclaimer.

(21) Appl. No.: 16/420,741

(22) Filed: May 23, 2019

(65) Prior Publication Data

US 2019/0344052 A1 Nov. 14, 2019

Related U.S. Application Data

(63) Continuation of application No. 14/942,198, filed on Nov. 16, 2015, now Pat. No. 10,357,637.

(30) Foreign Application Priority Data

Mar. 11, 2015 (AT) .............................. A 50197/2015
Nov. 6, 2015 (AT) .............................. A 50944/2015

(51) Int. Cl.
*A61M 25/10* (2013.01)
*A61M 1/36* (2006.01)
*A61B 17/00* (2006.01)

(52) U.S. Cl.
CPC .......... *A61M 25/10* (2013.01); *A61M 1/3659* (2014.02); *A61B 2017/00243* (2013.01);
(Continued)

(58) Field of Classification Search
CPC .. A61M 25/10; A61M 1/3659; A61M 27/002; A61M 2202/0208; A61M 2202/0413; A61B 2017/00243
See application file for complete search history.

(56) References Cited

U.S. PATENT DOCUMENTS 5,190,528 A * 3/1993 Fonger ................. A61M 25/01
604/164.11
5,314,418 A 5/1994 Takano et al.
(Continued)

FOREIGN PATENT DOCUMENTS

EP 2233169 A1 9/2010
WO 2014071161 A1 5/2014

*Primary Examiner* — Philip R Wiest
(74) *Attorney, Agent, or Firm* — Laurence A. Greenberg; Werner H. Stemer; Ralph E. Locher

(57) ABSTRACT

A cannula assembly for applying a flow cannula for the introduction, circulation or diversion of flow media, in particular blood, in the human or animal body. The flow cannula has a main portion and a tip portion. The tip portion is elastic and, in a functional position, is configured to protrude in an arc shape at an angle from the main portion, and in an application position, is held in the direction of the longitudinal extent of the main portion by a guide device. The flow cannula may be fitted for the indication of pulmonary hypertension and pulmonary insufficiency. The one of more flow cannulas so connected to the heart, for example, through an incision of the jugular vein or subclavian vein may be connected, on the outside, to a membrane ventilator, such as a Novalung®, with oxygen supply and/or additional pump support.

20 Claims, 6 Drawing Sheets

(52) U.S. Cl.
CPC ............... *A61M 2202/0208* (2013.01); *A61M 2202/0413* (2013.01)

(56) References Cited

U.S. PATENT DOCUMENTS

| | | | |
|---|---|---|---|
| 6,129,713 | A | 10/2000 | Mangosong et al. |
| 7,722,568 | B2 * | 5/2010 | Lenker .............. A61M 25/0662 |
| | | | 604/4.01 |
| 8,343,029 | B2 | 1/2013 | Farnan ................ A61M 1/3653 |
| | | | 600/16 |
| 8,460,168 | B2 | 6/2013 | Farnan |
| 10,357,637 | B2 * | 7/2019 | Klepetko .............. A61M 25/10 |
| 2009/0171276 | A1 | 7/2009 | Bednarek et al. |
| 2010/0249490 | A1 * | 9/2010 | Farnan ................ A61M 25/005 |
| | | | 604/103.1 |
| 2011/0160517 | A1 * | 6/2011 | Smith ................. A61M 1/3666 |
| | | | 600/16 |
| 2013/0131591 | A1 | 5/2013 | Berthiaume et al. |
| 2013/0317438 | A1 | 11/2013 | Ellingwood et al. |
| 2018/0126132 | A1 | 5/2018 | Heilman ............... A61M 39/24 |
| 2018/0264240 | A1 | 9/2018 | Heilman ............... A61M 39/24 |

* cited by examiner

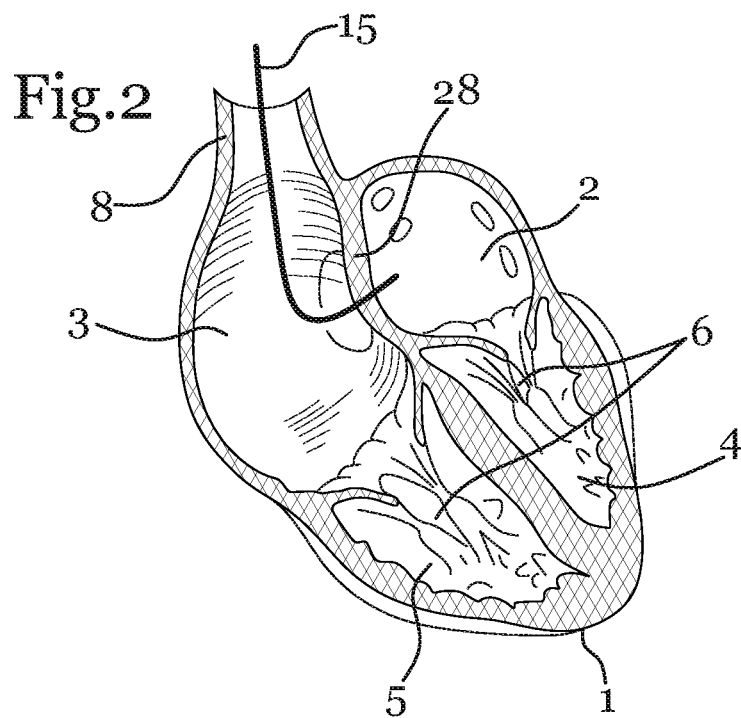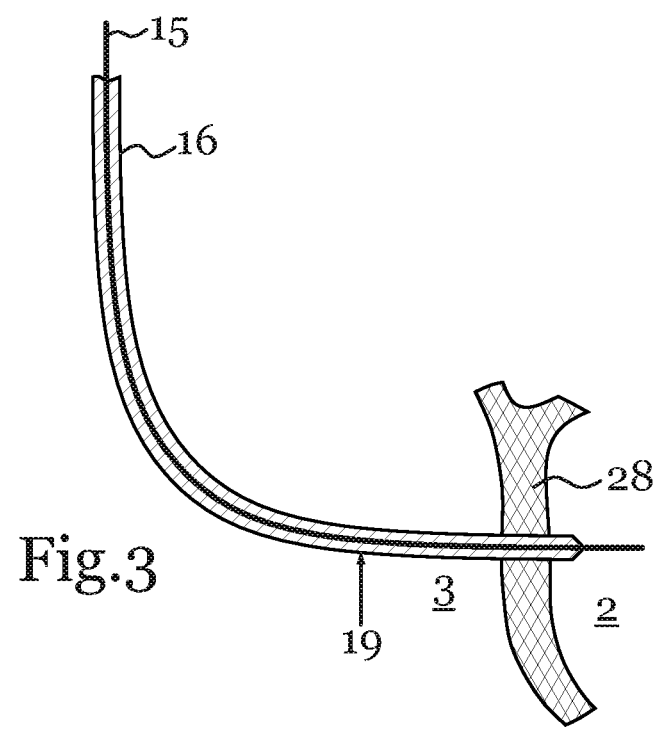

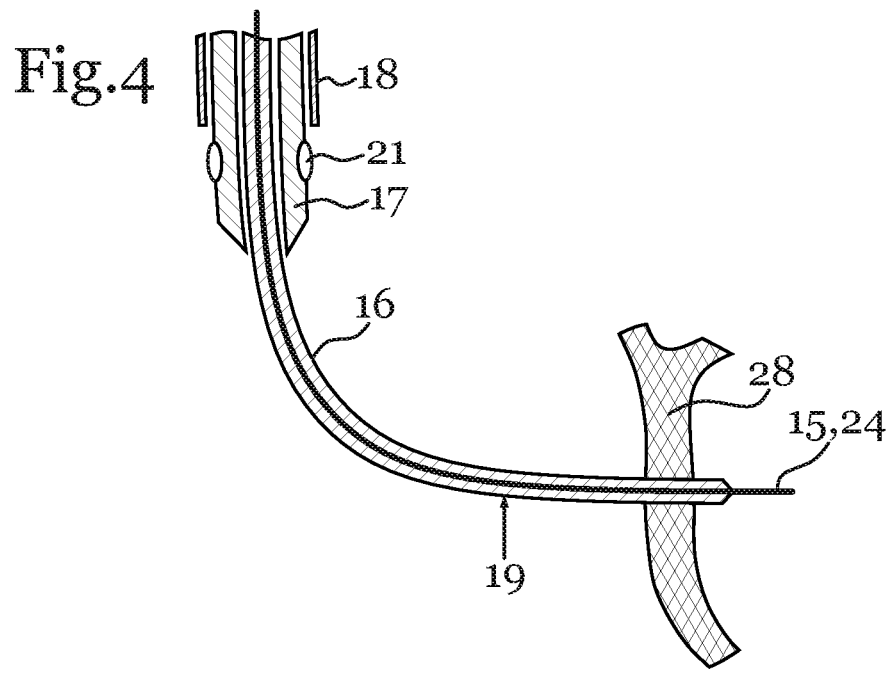
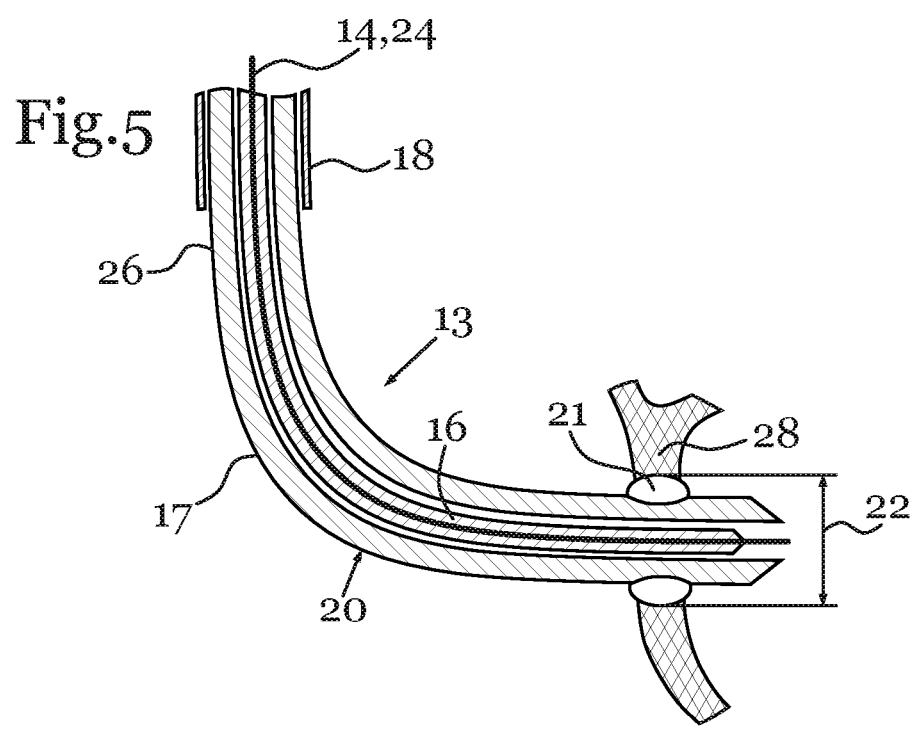

CANNULA ASSEMBLY FOR FITTING A FLOW CANNULA FOR INTRODUCING, CIRCULATING OR DIVERTING FLOW MEDIA, AND METHOD FOR EXTRACORPOREAL SUPPORT OF A PATIENT WITH PULMONARY HYPERTENSION OR PULMONARY INSUFFICIENCY

CROSS-REFERENCE TO RELATED APPLICATION

This is a continuation of U.S. patent application Ser. No. 14/942,198, filed Nov. 16, 2015; the application also claims the priority, under 35 U.S.C. § 119, of Austrian applications AT 50197/2015, filed Mar. 11, 2015, and AT 50944/2015, filed Nov. 6, 2015; the prior applications are herewith incorporated by reference in their entirety.

BACKGROUND OF THE INVENTION

Field of the Invention

The invention relates to a cannula assembly for applying a flow cannula for the introduction, circulation or diversion of flow media, in particular of blood in the human or animal body, wherein the flow cannula has a main portion and a tip portion. The invention further relates to a method for fitting cannulas and for extracorporeal support of patients with pulmonary hypertension.

Cannula assemblies and catheter systems have long been known in a wide variety of forms. Thus, it is also already known to insert cannulas, from an incision in the inguinal region, through the inferior vena cava into the right atrium of the heart. It is also known, with a catheter assembly of this kind, to use a puncture wire and the front end of the catheter to pierce the septum of the heart and thus fit the cannula in the left atrium of the heart. The trans-septal cannulation of the left atrium proves necessary or advantageous for the temporary treatment of severe pulmonary hypertension and for use in cases of conventional ECMO (extracorporeal membrane oxygenation) with serious saturation problems.

Severe end-stage pulmonary hypertension can only be treated by lung transplantation. However, in extreme cases, the waiting time for a suitable donor organ can only be bridged by mechanically assisting the pulmonary circulation. The established method for doing this at the present time is peripheral veno-arterial ECMO, but the latter poses a considerable risk to the patient.

With the present cannula assembly and its application, it is possible, by interventional trans-septal cannulation of the left atrium and additionally of the pulmonary artery, to produce a collateral circulation for the PH (pulmonary hypertension) pathway, as a result of which the patient can be stabilized for a longer period of time. In the aforementioned clinical picture, the procedure can comprise the following steps:

trans-septal cannulation of the left atrium (arterial return)
trans-tricuspid cannulation of the pulmonary artery (venous drainage) or normal venous cannulation,
connection of the cannulas to a conventional Novalung® (in trans-tricuspid cannulation) or to ILA-active (in venous cannulation) or to comparable appliances.

Whenever cannulas have to penetrate tissue regions, as is necessary when piercing the septum for cannulation of the left atrium for example, the problem is that the cannula is intended to orient the puncture tip of the required puncture wire as far as possible at a 90 degree angle to the tissue region. In the case of the cardiac septum, this is a minor problem if the cannulation is performed by a femoral approach, i.e. via the inferior vena cava, since the cannula guided into the left atrium and the puncture wire guided in the cannula come to lie approximately at a 90 degree angle to the septum. However, in the cannula assemblies known at present, it is not possible to create the preferred approach from the upper half of the body. The approach from above, for example via the superior vena cava, either by a cervical or subclavian route, is much more comfortable for the patient. The approach has greater permanence and is less likely to cause any problems. Moreover, the cannula assembly should be able to be anchored in the septum in order to prevent dislocation. The flow rate that is ultimately obtained must be sufficiently great. It is furthermore desirable to provide the cannula, and also the other parts of the cannula assembly, with antithrombotic properties. Preferably, the assembly should also offer the possibility of closing the defect in the atrial septum if removed.

Finally, the cannula assembly should also permit connection to the Novalung® system in a way that is permanent and stable, permits simple and rapid exchange of the Novalung® and restricts the physical activities of the patient to the least possible extent. Novalung® is a registered trademark of NovaLung GmbH of Heilbronn, Germany; it represents an interventional lung assist (iLA) device providing for oxygen and carbon dioxide gas exchange. The device is provided for supporting lung function of human beings. The device and related devices that satisfy the same or a similar function will be generically referred to herein as ventilators or membrane ventilators.

SUMMARY OF THE INVENTION

It is accordingly an object of the invention to provide a cannula device and an application method which overcome the above-mentioned and other disadvantages of the heretofore-known devices and methods of this general type and which provide for a cannulation with an approximately 90° puncture of a tissue portion, and in particular the fitting of a cannula through the septum of the heart.

With the foregoing and other objects in view there is provided, in accordance with the invention, a cannula assembly for applying a flow cannula for introducing, circulating or diverting a flow medium in a body, the cannula assembly comprising:
a flow cannula having a main portion and a tip portion;
a guide device;
said tip portion being elastic and being configured to assume a functional position and an application position; and
said tip portion, in the functional position, projecting from said main portion in an arc shape at an angle relative to said main portion; and
said tip portion, in the application position, being maintained by said guide device to project from said main portion in a direction of a longitudinal extent of said main portion.

In other words, the objects of the invention are achieved by the fact that the tip portion is elastic and, in a functional position, is designed to protrude in an arc shape at an angle from the main portion, and that the tip portion, in an application position, is maintained in the direction of the longitudinal extent of the main portion by a guide device.

Further features of the invention are, among others, the following:

The guide device preferably has a guide wire, a first dilation cannula, which can be pushed over the guide wire, a second dilation cannula, which can be pushed over the first dilation cannula, and a guide sleeve arranged over the second dilation cannula.

A further preferred feature is that the first and second dilation cannulas have their tip portions designed, in the same way as the tip portion of the cannula, protruding elastically in an arc shape at an angle from the respective main portions, wherein the first dilation cannula is guided by the guide wire, and the second dilation cannula is guided by the first dilation cannula arranged therein and is guided along the longitudinal extent of the guide wire.

It is furthermore advantageous if the guide sleeve, during the application, is removable from the tip portion, such that the latter can adopt the arc-shaped curvature, and the guide sleeve is removable in its entirety and replaceable by the cannula, after which the guide wire and the first and second dilation cannulas are removable from the cannula, such that the entire internal cross section of the cannula is freed.

The invention can further be characterized in that the tip portion of the second dilation cannula has, adjacent to the tip, a dilation balloon whose diameter in the inflated state corresponds to the external diameter of the cannula and whose diameter in the relaxed state is equal to or smaller than the internal diameter of the cannula.

In the tip portion, the cannula can have a locking device, preferably a balloon, for fixing the cannula.

The first and second dilation cannulas and the cannula are, in the unsupported state, preferably bent at an angle of 20° to 100°, preferably 60° to 95°, particularly preferably 90°, in the tip portion.

Preferably, the assembly is designed for trans-septal cannulation of the left atrium of the heart by a cervical approach for the trans-atrial puncture.

The surfaces of the parts of the assembly are preferably made antithrombotic, in particular heparinized.

The invention also relates to the use of the assembly for trans-septal cannulation of the left atrium of the human heart by a cervical approach, and furthermore to a method for fitting cannulas and for extracorporeal support of patients with pulmonary hypertension, or also other forms of respiratory insufficiency as defined in the claims.

With the above and other objects in view there is also provided, in accordance with the invention, a method of fitting a cannula into a body (e.g., a human or other animal body), the method comprising:
  providing a cannula assembly with a flow cannula and inner dilation cannulas, the flow cannula having a main portion and a tip portion, wherein the tip portion is elastic and, in a functional position, projects from the main portion in an arc shape at an angle relative to the main portion, and wherein the tip portion, in an application position, is held by a guide device to project in a direction of a longitudinal extent of the main portion;
  providing a catheter with a guide wire guided inside the catheter;
  inserting a sling through an incision at the jugular vein or subclavian vein and advancing the sling to the femoral vein;
  guiding the catheter with the guide wire from the femoral vein in the inguinal region to the right ventricle, and pushing the guide wire through the septum and anchoring the guide wire there;
  subsequently removing the catheter;
  using the sling to pull the guide wire up to the jugular vein or subclavian vein;
  fitting the cannula assembly over the guide wire from the jugular vein or subclavian vein; and
  after the flow cannula has been fitted, removing the inner dilation cannulas and the guide wire.

In accordance with an added feature of the invention, there is also provided a method for extracorporeal support of patients with pulmonary hypertension. As described above, a flow cannula is provided as a left atrial cannula for circulation of blood into the left atrium of the heart, and a flow cannula is provided as a pulmonary cannula for diverting blood from the pulmonary artery. Then, a membrane ventilator (e.g., a Novalung® membrane or a similar appliance) with the associated oxygen supply is provided, optionally with pump assistance and the connection cannulas.

In accordance with an additional feature of the invention, the left atrial cannula is guided out of the body through the incision from the right subclavian vein and the pulmonary cannula is guided out of the body from the left subclavian vein incision and they are connected to the Novalung® membrane via the connection cannulas.

In accordance with a concomitant feature of the invention, there is provided a method for extracorporeal support of a patient with pulmonary insufficiency. As described above, a flow cannula is fitted as a left atrial cannula for circulation of blood into the left atrium of the heart, and a cannula for venous blood removal is fitted, for example, into the superior vena cava. Then the cannulas are connected to the membrane ventilator and, optionally, to an extracorporeal pump, preferably a centrifugal pump, in order to replace or to support the pulmonary function.

Other features which are considered as characteristic for the invention are set forth in the appended claims.

Although the invention is illustrated and described herein as embodied in a cannula device and an application method, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIGS. 2 to 7 show schematic stepwise representations of the structure of the assembly according to the invention and of its use in the human heart for fitting the flow cannula into the left atrium of the heart;

DETAILED DESCRIPTION OF THE INVENTION

Figure 1:
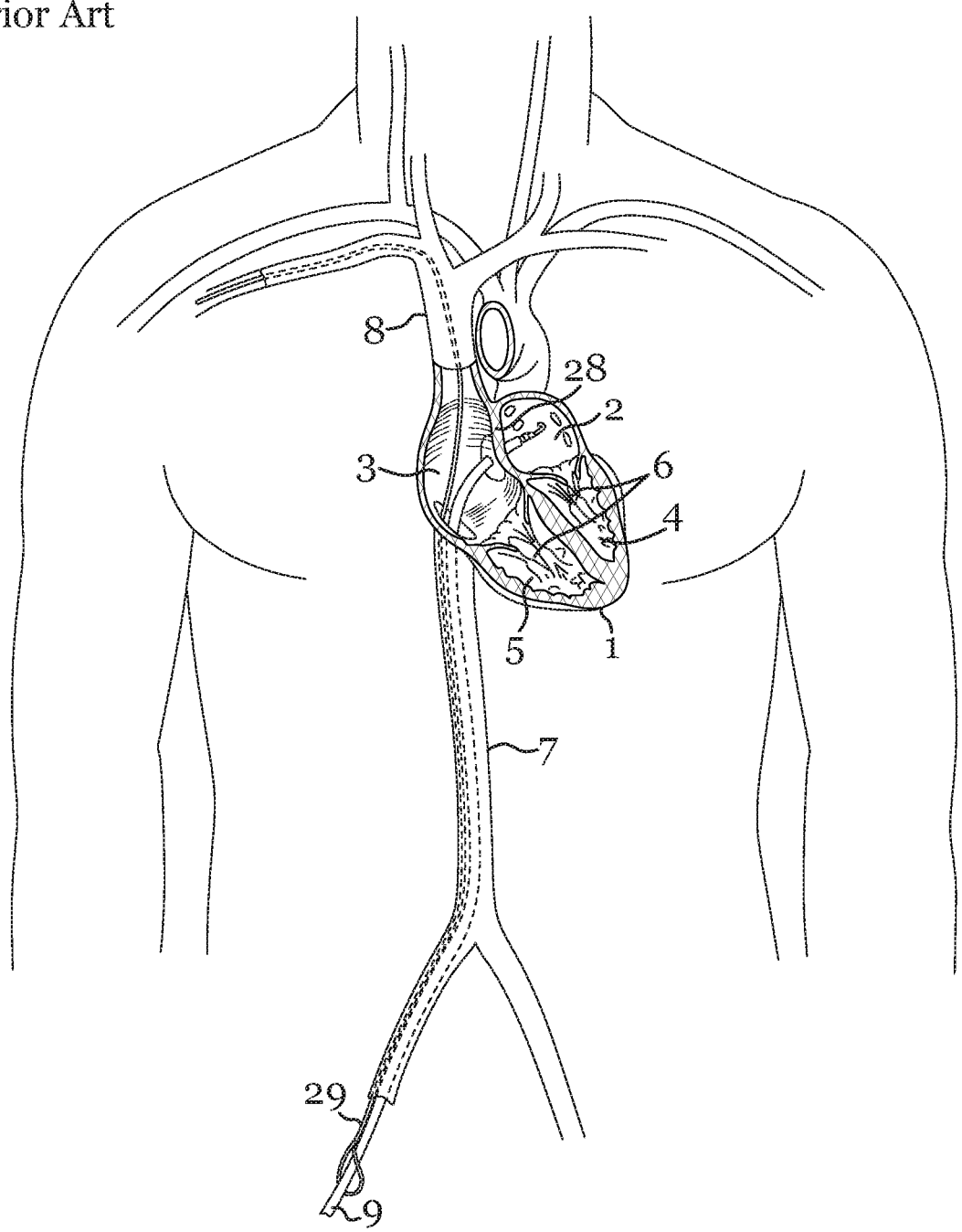
FIG. 1 shows a schematic representation of a cannula assembly according to the prior art.

Referring now to the figures of the drawing in detail and first, particularly, to FIG. 1 thereof, there is shown a prior art embodiment as disclosed, for example, in U.S. Pat. No. 8,343,029 B2. A catheter 9 is preferably inserted through an incision in the inguinal region and pushed upward through the inferior vena cava 7 into the right atrium 3 of the heart 1 and, with its tip portion, penetrates the septum 28, such that the catheter ends in the left atrium 2. However, this position of the catheter, and of the cannula which is inserted with it and passes through the body from the inguinal region to the heart, has the disadvantages described at the outset.

FIG. 1 also shows, as prior art, an inserted sling 29 which can be guided from the vein in the area of the clavicle down through the superior vena cava 8, in order that a guide wire provided in the catheter 9 can be pulled upward. However, it is thus not possible to insert a cannula with a suitable volume and a diameter of approximately 5 to 9 mm into the left atrium.

The procedure according to the invention, using the cannula assembly according to the invention, is explained with reference to FIGS. 2 to 7.

In a first step, as per FIG. 1, the guide wire 15 with its puncture tip is pushed through the septum 28, in a known manner by means of the catheter 9, into the left atrium 2. Then, after removal of the catheter 9, the guide wire is pulled upward with the sling 29 into the jugular vein or the subclavian vein, wherein the end of the guide wire is guided out of the body through an opening of the vein.

FIG. 2 shows how the guide wire 15 is guided from the superior vena cava 8 to the left atrium 2. This guide wire (the word "wire" does not imply any limitation in terms of the material) can be very soft and pliable.

If it is found that the guide wire 15 is too soft in order to properly guide the first dilation cannula 16, the guide wire can be replaced by a stiffer guide wire, by means of a soft tube, also called sheet, being pushed over the soft wire as far as into the septum, the soft wire being removed, and the stiff wire being pushed in as a new guide wire 24 as far as the left atrium.

However, a stiff wire can also be pulled in later when the following dilation cannulas are already fitted.

According to FIG. 3, in a next step, the first dilation cannula 16 is pushed in over the guide wire 15 or 24, and the first dilation cannula 16 has a tip portion 19 which is already bent with sufficient tensioning (but only to such an extent that it can still be straightened by the guide wire), such that the first dilation cannula comes to lie at an angle of about 90° against the septum 28 and can be pushed through the septum 28. This therefore permits a first and still relatively gentle and narrow approach to the left atrium of the heart from above.

According to FIG. 4, in the next step, a second dilation cannula 17 is pushed over and along the first dilation cannula 16. In the tip portion 20, the second dilation cannula 17 is also already bent at about 90° with respect to the main portion 26, with sufficient pretensioning. However, with the aid of the guide sleeve 18 arranged on the outside, the tip portion 20 of the second dilation cannula is kept straight, in such a way that the cannula can be advanced straight over the entire main portion of the first dilation cannula 16. The first dilation cannula also contributes to stiffening the second dilation cannula. As soon as the second dilation cannula reaches the position as per FIG. 4, the physician prevents the guide sleeve 18 from following the advance movement of the second dilation cannula, such that the tip portion leaves the guide sleeve 18 and, in accordance with the pre-bending, assumes the bent position as shown in FIG. 5. The unsupported position of the cannulas as per FIG. 5 is designated here as the functional position, whereas the supported, straightened position of the respective tip portions is designated as the application position.

As is likewise shown in FIG. 5, the second dilation cannula 17 is also pushed through the septum 28 into the left atrium 2, wherein a dilation balloon 21 is preferably provided in the tip portion of the second dilation cannula, which dilation balloon 21 can be inflated in a known manner in order to widen the hole in the septum 28 for the cannula that is finally to be inserted.

In the next step, the guide sleeve 18 is pulled out from the dilation cannulas, and the cannula 10 that is ultimately required is pushed in, which cannula 10 can likewise have an already bent tip portion, and, during the application, when pushing in, the necessary stiffness is provided by the two dilation cannulas that have been introduced beforehand, such that the pre-bending is overcome and the cannula 10 can be pushed inward in a straight shape. As soon as the bending as per FIG. 6 is reached, the cannula 10 can easily follow the bending and can be pushed through the septum into the left atrium.

In order to lock the cannula in place, a locking balloon is shown which, as locking device 27, is balloon-shaped. However, the locking can also be achieved by other means, e.g. by braces.

Figure 6:
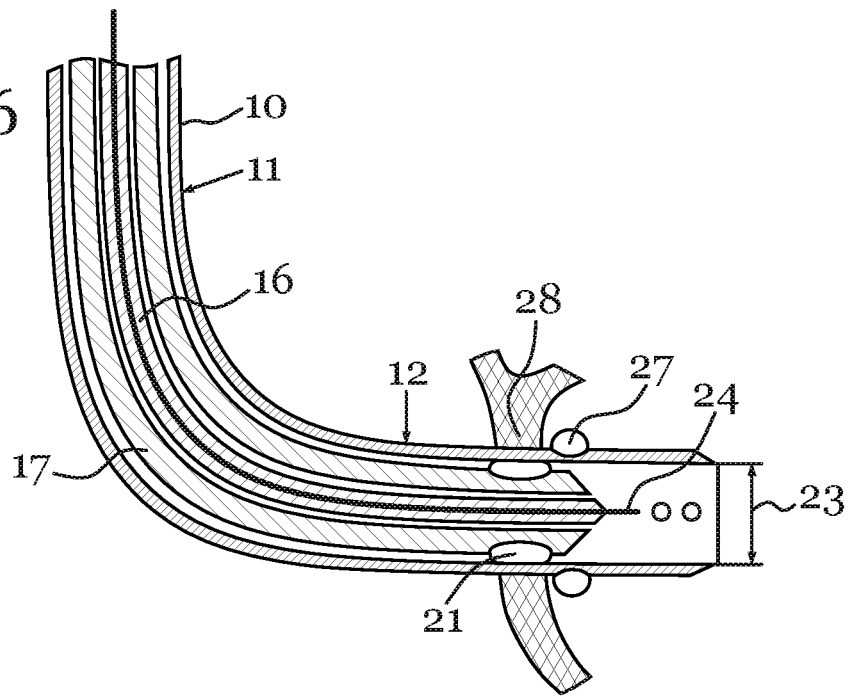

As can likewise be seen in FIG. 6, the dilation balloon 21 of the second dilation cannula 17 can be relaxed by releasing the air pressure, in such a way that the external diameter in the balloon area corresponds approximately to the internal diameter of the cannula 10. The path through the septum is thus freed for the cannula 10. In the inflated state as per FIG. 5, the balloon 21 has an external diameter which corresponds to the external diameter of the cannula 10 and thus widens the hole in the septum, in such a way that the cannula 10 can be easily pushed in.

Figure 7:
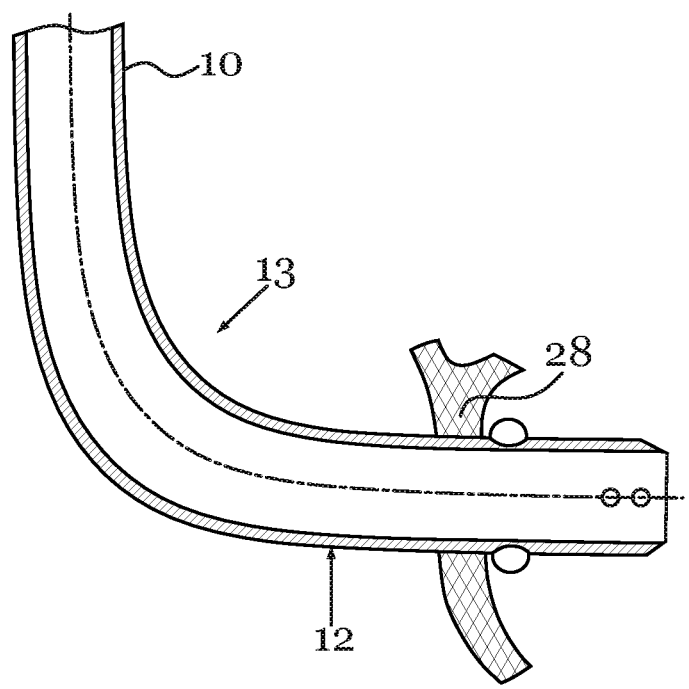

To end with, FIG. 7 shows the final position of the cannula 10 from which all the inner parts, namely guide wire 15 or 24 and both dilation cannulas 16, 17, have been pulled out. Thus, the entire cross-sectional volume of the flow cannula 10 is available as a left atrial cannula (LA cannula) in order to produce the desired flow rates and flow conditions.

The number of the dilation cannulas to be pushed over one another is not limited to two. If the dilation balloon 21 is to be avoided, it is also possible for a third or a fourth cannula with the above-mentioned properties to be pulled over in order to obtain the necessary widening of the opening in the septum and the required cross section of flow in the finally inserted flow cannula 10. The dilation cannulas preferably have a free inner cross section, which allows the cannula to be pushed over the inner guide wire or over the inner dilation cannula.

Figure 8:
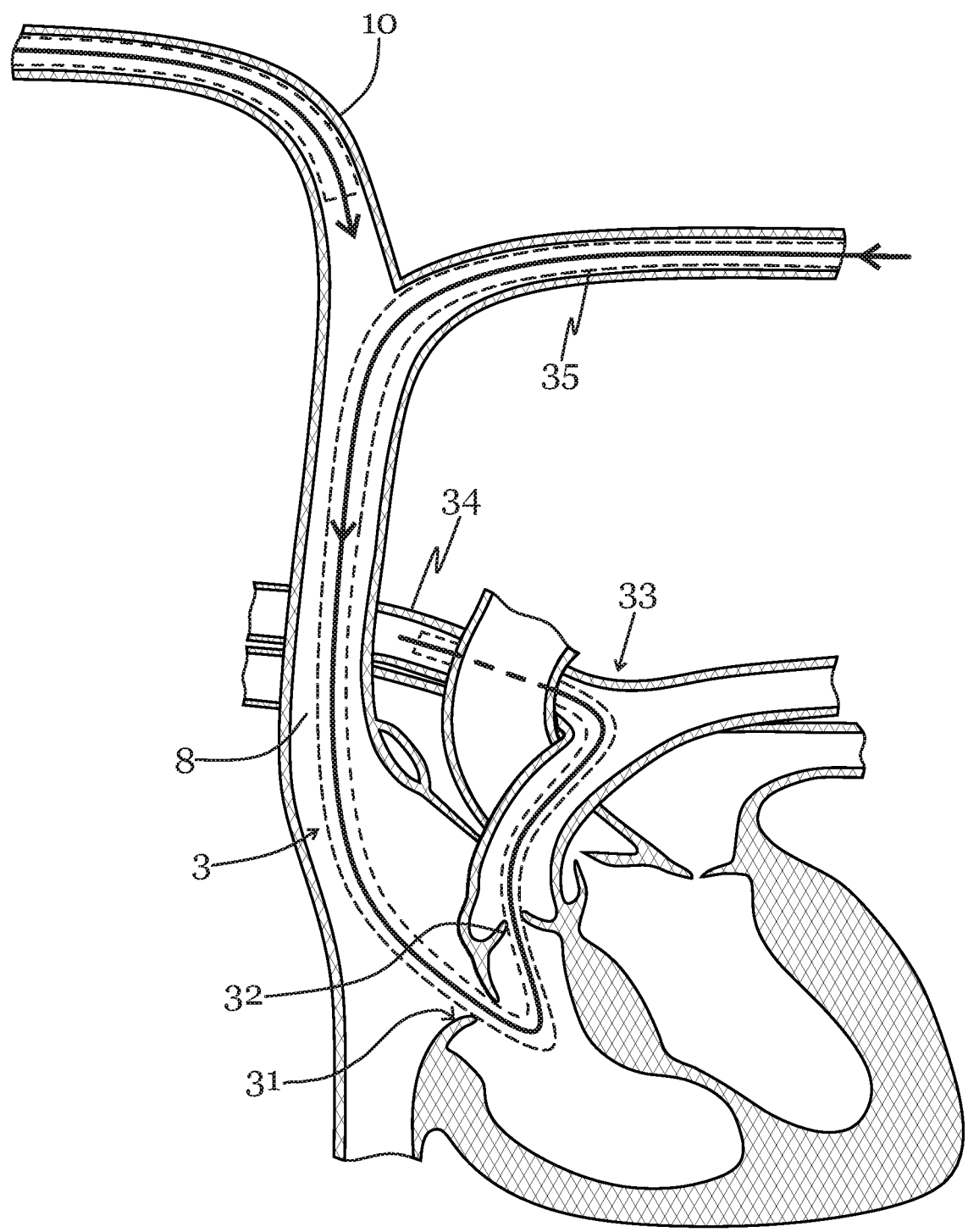
FIG. 8 shows another schematic representation of the heart in order to explain the route of an additional pulmonary catheter.

FIG. 8 is a schematic representation of the assembly of a further flow cannula as a pulmonary cannula 35 for cannulation of the pulmonary artery 33. A conventional pulmonary catheter, which is relatively soft and carries a balloon, is inserted via the superior vena cava 8. A pulmonary catheter of this kind can be equipped with a guide wire, such that the guide wire, with the catheter, is washed by the natural blood stream through the right atrium 3, through the tricuspid valve 31 into the right ventricle, and from there through the pulmonary valve 32 into the pulmonary artery 33. The guide wire should preferably be inserted into the right pulmonary artery 34.

As soon as the guide wire has adopted its desired position, it is possible, in the manner described above, for one or more cannulas to be inserted in successive stages, wherein the guide function is taken over by the guide wire, and the cannulas, by being suitably flexible, are also able to bend to the desired shape.

Figure 9:
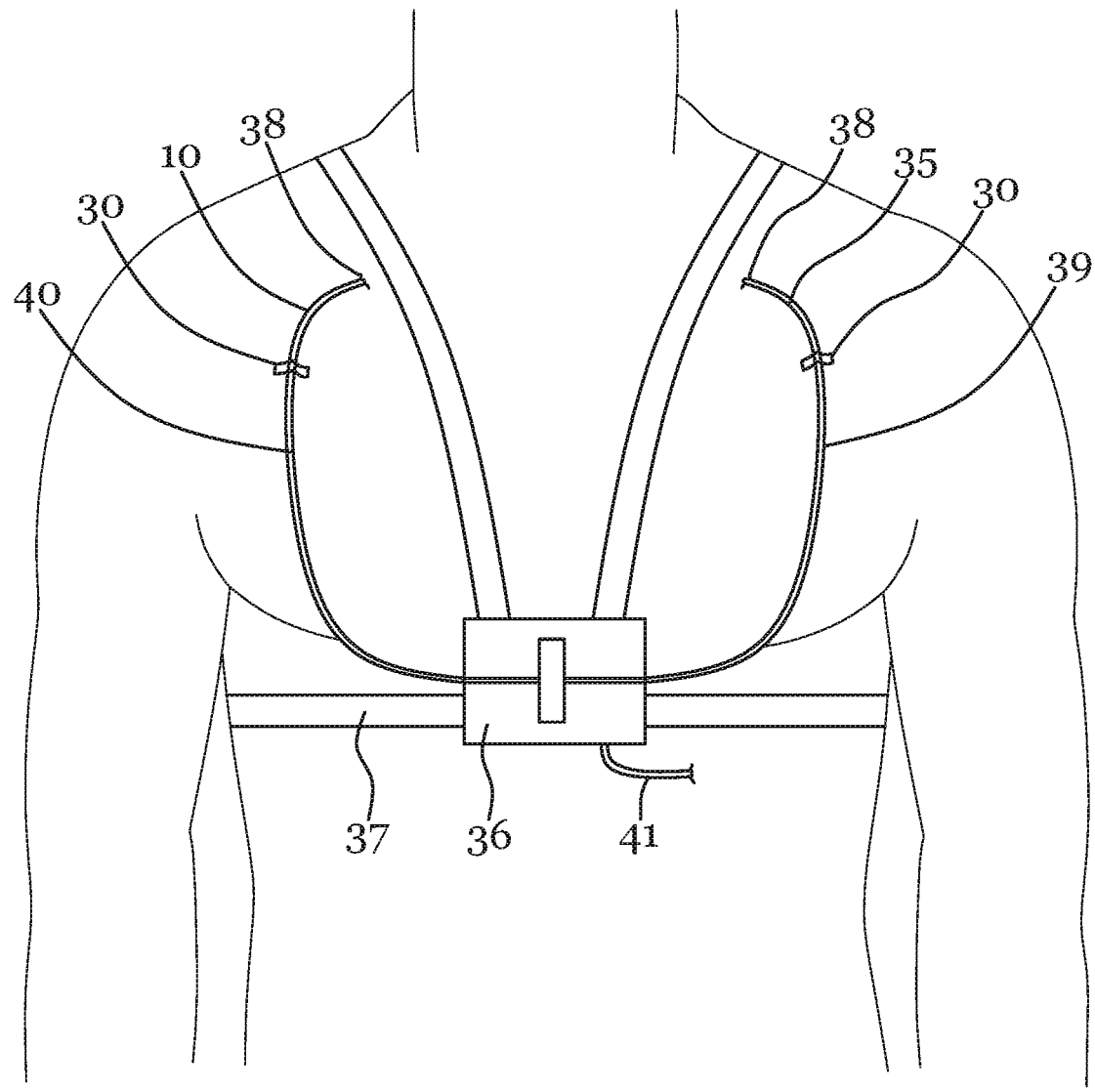
FIG. 9 shows the assembly of a device for extracorporeal membrane oxidation.

With the aid of the first flow cannula 10 (LA cannula) inserted into the left atrium as per FIGS. 2 to 7, and the pulmonary cannula 35 inserted into the pulmonary artery as per FIG. 8, it is possible to divert blood from the pulmonary artery into the left atrium, and, by way of suitable hose connections outside the body, it is possible to attach a portable device in which $CO_2$ is removed from the blood and $O_2$ is added. This is shown in FIG. 9.

In FIG. 8, the flow cannula 10 (LA cannula) leading to the left atrium is indicated only in the upper portion. The full position can be seen from FIGS. 2 to 7.

Alternatively, instead of removing blood from the pulmonary artery, venous blood can be removed, for example from the superior vena cava. With the aid of a pump (e.g., a centrifugal pump), the venous blood can be returned via the Novalung® or via a comparable device and the LA cannula into the left atrium of the heart. This alternative is preferred for those cases when the pulmonary hypertension is not excessively high and the lung function is intended to be replaced or assisted.

The procedure and further embodiments are described below:

End-stage pulmonary hypertension leads to right-ventricular failure. When drug treatment has been exhausted, this failure can be prevented only by mechanical circulatory support. All prior art methods are either performed surgically or are suitable for use only for a short period of time, with no possible mobility of the patient.

The percutaneous insertion of cannulas by an approach from the upper half of the body, as per the invention, makes it possible to establish a permanent access. In connection with a membrane that removes $CO_2$ and adds $O_2$ (e.g., Novalung®, iLA=interventional lung assist), blood can be diverted from the pulmonary artery into the left atrium. This makes it possible to reduce the pressure in the pulmonary artery and at the same time to maintain the oxygen saturation of the arterial blood. The blood flow is purely passive, driven by the high pressure efficiency between pulmonary artery and left atrium, or, if this is not sufficient, by an additional pump drive, for example by means of a centrifugal pump.

Limited mobility of the patients can be achieved by virtue of the suitable configuration, according to the invention, of the cannulas, in conjunction with a carrier bag structure.

To realize this concept, the following are needed:
a suitable cannula for diverting the blood from the pulmonary artery, namely the pulmonary cannula 35,
a suitable possibility of connecting this cannula to a connector 30, as is known,
a Novalung membrane 36 (with or without pump assistance) or a comparable appliance,
a suitable possibility of connection 30 of the Novalung to the cannula for returning the blood to the left atrium, namely the LA cannula 10.

Furthermore, the carrier bag structure 37 is provided.

The pulmonary cannula is inserted by percutaneous puncture of the subclavian vein, preferably of the left subclavian vein. To do this, the following steps are necessary:
puncturing of the vein at the incision 38
insertion of a first soft guide wire
inserting over this a catheter with a balloon at the tip. This is similar to a conventional pulmonary catheter but suitable for serving as a guide for a stiffer guide wire to be introduced therein. By inflation of the balloon, this catheter is washed passively by the blood flow through the superior vena cava, the tricuspid valve 31 and the pulmonary valve 32 into the pulmonary artery. Thereafter, a second stiff guide wire inside the balloon catheter is advanced into the pulmonary artery, and the balloon catheter is removed.

The actual pulmonary cannula is then inserted over the guide wire lying in the pulmonary artery and is positioned there. The guide wire is then removed. If necessary, as an intermediate step, a guide cannula with a wider cross section can also be inserted.

At its proximal end, the pulmonary cannula 35 has a connection device 30, which permits quick, simple and stepless connection to the iLA device (e.g., Novalung®). This is achieved using a suitable first connection cannula 39, such that the necessary configuration is achieved in order to permit direct and unobstructed access to the iLA device.

The iLA device used corresponds to the conventionally used membrane devices. It can be placed in a suitable carrier device 37 in front of the patient's chest, such that the patient, although restricted, is still mobile; see FIG. 9. The required oxygen supply takes place through an oxygen hose 41 from a non-illustrated, separate oxygen reservoir. If an iLA active with a pump system is used, it is possible for the entire device to be mounted on a support console. Accordingly, the connectors are to be set up in another configuration suitable for this purpose, as is familiar to any medical technician.

Similarly, a second connection cannula 40 is needed that permits the necessary connection between iLA device (Novalung) 36 and left atrial cannula (LA cannula 10).

The left atrial cannula is inserted as per FIG. 2 to FIG. 7 and is then guided from above through the superior vena cava 8 into the heart as far as the left atrium.

This assembly can be provided for temporary use, for example as a bridging means prior to a transplant, or to improve the overall state of health by general recovery of the patient, possibly also after an operation. However, it can also serve as a permanent support for patients who have no prospect of improvement and are not candidates for a transplant.

The following is a summary list of reference numerals and the corresponding structure used in the above description of the invention:

1 heart
2 left atrium
3 right atrium
4 left ventricle
5 right ventricle
6 cardiac valve
7 inferior vena cava
8 superior vena cava
9 catheter
10 flow cannula (LA cannula)
11 main portion of cannula
12 tip portion of cannula
13 angle
14 guide device
15 soft guide wire
16 first dilation cannula
17 second dilation cannula
18 guide sleeve
19 tip portion of first dilation cannula
20 tip portion of second dilation cannula
21 dilation balloon
22 diameter of dilation balloon when inflated
23 diameter of dilation balloon when relaxed
24 stiff guide wire
25 main portion of first dilation cannula
26 main portion of second dilation cannula
27 locking device
28 septum 29 sling
30 connector
31 tricuspid valve
32 pulmonary valve
33 pulmonary artery
34 right pulmonary artery
35 pulmonary cannula
36 Novalung® iLA ventilator membrane
37 support frame
38 incision
39 connection cannula
40 connection cannula
41 oxygen supply hose

The invention claimed is:

1. A cannula assembly for applying a flow cannula for introducing, circulating or diverting a flow medium in a body, the cannula assembly comprising:
a flow cannula having a main portion and a tip portion;
a guide device;
said tip portion being elastic and being configured to assume a functional position and an application position; and
said tip portion, in the functional position, projecting from said main portion in an arc shape at an angle relative to said main portion; and
said tip portion, in the application position, being maintained by said guide device to project from said main portion in a direction of a longitudinal extent of said main portion;
said guide device including:
a guide wire;
a first dilation cannula to be pushed over said guide wire;
a second dilation cannula to be pushed over said first dilation cannula;
a guide sleeve arranged over said second dilation cannula; and
one or more further dilation cannulas to be pushed over said second dilation cannula, and said guide sleeve is arranged over an outermost said dilation cannula.

2. The assembly according to claim 1, wherein each of said first dilation cannula, said second dilation cannula, and optional further dilation cannulas, if provided, has a respective tip portion designed, in the same way as said tip portion of said flow cannula, protruding elastically in an arc shape at an angle from the respective main portion, wherein said first dilation cannula is guided by said guide wire, and said second dilation cannula and any optional said dilation cannula, is guided by said first dilation cannula arranged therein and is guided along the longitudinal extent of said guide wire.

3. The assembly according to claim 1, wherein, during application, said guide sleeve is removable from said tip portion, to allow said tip portion to adopt the arc-shaped curvature, and said guide sleeve is removable in its entirety and replaceable by said flow cannula, after which said guide wire and any said dilation cannulas are removable from said flow cannula, to free up an entire internal cross section of said flow cannula.

4. The assembly according to claim 1, wherein said flow cannula carries a locking device at said tip portion for fixing the cannula.

5. The assembly according to claim 4, wherein said locking device is an inflatable balloon.

6. The assembly according to claim 1, wherein said tip portions of said first dilation cannula, said second dilation cannula, any optional, further dilation cannulas, and said flow cannula are bent, in an unsupported state, at an angle of 20° to 100° relative to said main portion.

7. The assembly according to claim 6, wherein said tip portions are bent, in the unsupported state, at an angle of 60° to 95° relative to said main portion.

8. The assembly according to claim 6, wherein said tip portions are bent, in the unsupported state, at an angle of substantially 90° relative to said main portion.

9. The assembly according to claim 1, configured for trans-septal cannulation of a the left atrium of a heart by an approach via the superior vena cava for a trans-atrial puncture.

10. The assembly according to claim 1, wherein surfaces of components of the assembly are rendered antithrombotic.

11. The assembly according to claim 10, wherein the surfaces of the components are heparinized.

12. The assembly according to claim 1, wherein said tip portion of said second dilation cannula or an outermost dilation cannula has, adjacent to said tip, a dilation balloon with a diameter in an inflated state that is equal to an external diameter of said cannula and with a diameter in a relaxed state that is smaller than or equal to an internal diameter of said cannula.

13. A method of fitting a cannula into a body, the method comprising:
providing a cannula assembly with a flow cannula and inner dilation cannulas, the inner dilation cannulas having a second dilation cannula to be pushed over a first dilation cannula, and one or more further dilation cannulas pushed over the second dilation cannula, and a guide sleeve being arranged over an outermost the dilation cannula, the flow cannula having a main portion and a tip portion, wherein the tip portion is elastic and, in a functional position, projects from the main portion in an arc shape at an angle relative to the main portion, and wherein the tip portion, in an application position, is held by a guide device to project in a direction of a longitudinal extent of the main portion;
providing a catheter with a guide wire guided inside the catheter;
inserting a sling through an incision at the jugular vein or subclavian vein and advancing the sling to the femoral vein;
guiding the catheter with the guide wire from the femoral vein in the inguinal region to the right ventricle, and pushing the guide wire through the septum and anchoring the guide wire there;
subsequently removing the catheter;
using the sling to pull the guide wire up to the jugular vein or subclavian vein;
fitting the cannula assembly over the guide wire from the jugular vein or subclavian vein; and
after the flow cannula has been fitted, removing the inner dilation cannulas and the guide wire.

14. The method according to claim 13, wherein the flow cannula is fitted to enable an introduction, circulation or diversion of blood in the human or animal body.

15. The method according to claim 13, wherein the flow cannula is fitted upon indication of pulmonary hypertension.

16. A method for extracorporeal support of a patient with pulmonary hypertension, the method comprising:
carrying out the method according to claim 13 to provide a flow cannula as a left atrial cannula for circulation of blood into the left atrium of the heart and a flow cannula as a pulmonary cannula for diverting blood from the pulmonary artery; and providing an membrane ventilator with an associated oxygen supply and connecting the left atrial cannula and the pulmonary cannula to the membrane ventilator.

17. The method according to claim 16, wherein the left atrial cannula is guided out of the body through the incision from the right subclavian vein and the pulmonary cannula is guided out of the body from the left subclavian vein incision and the flow cannulas are connected to the membrane ventilator via the connection cannulas.

18. A method for extracorporeal support of a patient with pulmonary insufficiency, the method comprising:
   carrying out the method according to claim 12 to fit a flow cannula as a left atrial cannula for circulation of blood into the left atrium of the heart, and to fit a flow cannula for venous blood removal (e.g., in the superior vena cava); and
   connecting a membrane ventilator and, optionally, to an extracorporeal pump in order to replace or to support the pulmonary function.

19. A cannula assembly for applying a flow cannula for introducing, circulating or diverting a flow medium in a body, the cannula assembly comprising:
   a flow cannula having a main portion and a tip portion;
   a guide device, said guide device including:
      a guide wire;
      a first dilation cannula to be pushed over said guide wire;
      a second dilation cannula to be pushed over said first dilation cannula;
      a guide sleeve arranged over said second dilation cannula; and
      one or more further dilation cannulas to be pushed over said second dilation cannula, and said guide sleeve is arranged over an outermost said dilation cannula;
   said tip portion being pre-bent and elastic, and being configured to assume a functional position and an application position; and
   said tip portion, in the functional position, projecting from said main portion in an arc shape at an angle relative to said main portion; and
   said tip portion, in the application position, being maintained by said guide device to project from said main portion in a direction of a longitudinal extent of said main portion.

20. The assembly according to claim 19, wherein:
each of said first dilation cannula, said second dilation cannula, and said optional further dilation cannulas, if provided, has a respective tip portion that is pre-bent with sufficient tensioning, in the same way as said tip portion of said flow cannula, and that protrudes elastically in an arc shape at an angle from the respective main portion, wherein said first dilation cannula is guided by said guide wire, and said second dilation cannula and any optional said dilation cannula, is guided by said first dilation cannula arranged therein and is guided along the longitudinal extent of said guide wire.

* * * * *